United States Patent [19]

Leitner

[11] 4,276,781

[45] Jul. 7, 1981

[54] METHOD OF AND ARRANGEMENT FOR ADAPTING A HEARING AID

[75] Inventor: Harald Leitner, Neubörnsen, Fed. Rep. of Germany

[73] Assignee: U.S. Philips Corporation, New York, N.Y.

[21] Appl. No.: 78,545

[22] Filed: Sep. 24, 1979

[30] Foreign Application Priority Data

Oct. 9, 1978 [DE] Fed. Rep. of Germany ....... 2843923

[51] Int. Cl.³ .......................... A61B 5/12; H04R 25/00
[52] U.S. Cl. ...................................... 73/647; 179/1 N
[58] Field of Search ................. 73/647, 645, 646, 648; 179/1 N, 107 R; 128/746

[56] References Cited

U.S. PATENT DOCUMENTS

| | | | |
|---|---|---|---|
| 3,784,745 | 1/1974 | Stearns | 179/1 N |
| 3,784,750 | 1/1974 | Stearns et al. | 179/1 N |

FOREIGN PATENT DOCUMENTS 2719796  11/1978  Fed. Rep. of Germany ............. 73/646

*Primary Examiner*—Stephen A. Kreitman
*Attorney, Agent, or Firm*—Bernard Franzblau

[57] ABSTRACT

A method of and apparatus for accurately adjusting a hearing aid. First a wide-band reference signal of relatively low sound level, e.g. 40 to 50 dB, is reproduced via a loudspeaker. The gain of the hearing aid is adjusted so that the person wearing it can just hear this reference signal. Then, in addition to the reference signal, a periodically recurring narrow-band signal having a duration of approximately 150 msecs is reproduced and the range of the optimum sound-level of speech is determined for different central frequencies of this narrow-band signal. The range thus determined is compared with the range of optimum sound-level of speech for persons with normal hearing and subsequently the setting of the hearing aid is corrected so that the sound level experienced as a pleasing sound level of speech by the user of the hearing aid falls within the sound-level range which is pleasing to persons with normal hearing.

8 Claims, 4 Drawing Figures

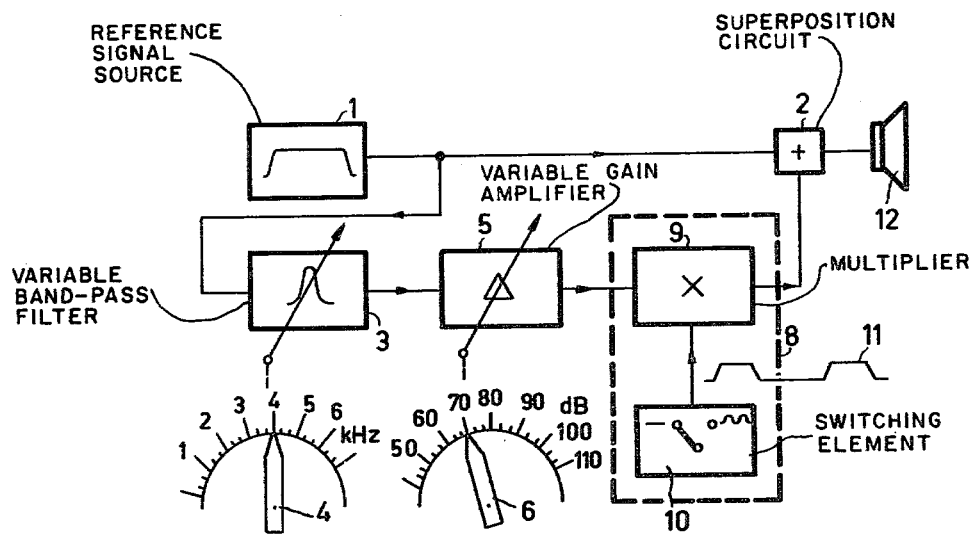
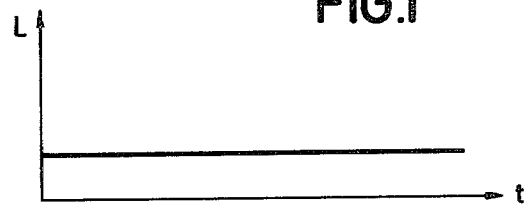
FIG.1
FIG.2a
FIG.2b
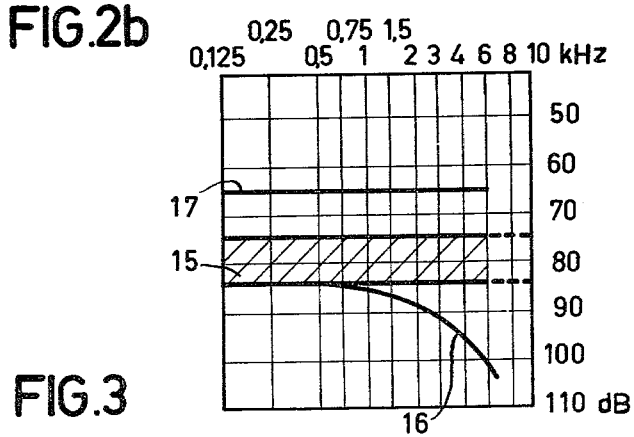
FIG.3

METHOD OF AND ARRANGEMENT FOR ADAPTING A HEARING AID

The invention relates to a method of adapting a hearing aid by means of a series of acoustic test signals of variable frequency and sound level. The sound level which is pleasing to the user of the hearing aid is determined as a function of the frequency and is compared with the sound level range (reference sound-level) which is pleasing to persons with normal hearing abilities, after which the gain of the hearing aid as a function of the frequency is changed so that the sound-level found to be pleasing corresponds to the reference sound-level. The invention also relates to an arrangement for carrying out this method.

In practice the individual adaptation or matching of the transmission characteristics of a hearing aid to the nature of the hearing defect of the user of said aid is generally effected empirically by audiometrists. The adaptation then depends on the skill and experience of the audiometrist, takes a lot of time and nevertheless often yields unsatisfactory results. However, a method is known ("Basic Principles of Otometry", Victoreen, J.; Springfield, Ill.; 1973) which is said to provide reproducible results. A series of exponentially decreasing sinusoidal acoustic test signals is then presented to the user, the amplitude of said signals being reduced by approx. 10% every period. The frequency of these signals as well as their sound level is variable. At different frequencies the sound level is varied and the patient indicates at which sound level the test signal is most pleasing to him. This value is plotted in a diagram and the procedure is repeated for other frequencies. The resulting curve, which represents the sound level which is pleasing to the relevant patient, is compared with the reference sound-level range which is pleasing to persons with normal hearing abilities. This range is situated at approximately 72 dB. The gain of the hearing aid is then varied so that the sound level experienced as pleasing by the patient at least substantially corresponds to the reference sound-level range.

However, it has been found that this method does not yield reproducible results either. This may be attributed to varying levels of background noise at the test location. Apparently there are also physiological and psychological influences. When the patient is told in advance that he should determine the sound level at which speech is most pleasing to him, other values are obtained than when this is not told in advance. The patient experiences the test signals as "clicks", which do not at all resemble speech signals. Test signals of higher frequency have only a very short duration. The amplitude of a 4 kHz test signal for example decreases by 40 dB within 11 msecs. However, in such a short time the response time of the diaphragm of the ear of the patient being examined has not yet elapsed. In hearing aids with automatic gain control the control cannot respond correctly within such a duration of the test signal.

It is an object of the present invention to provide a method for the individual adaptation of the transmission characteristics of a hearing aid to the user of said aid which yields reproducible and practical results.

Starting from a method of the type mentioned in the preamble, this object is achieved in accordance with the invention in that first of all a wide-band reference signal of predetermined constant level is presented to the user. The gain of the hearing aid is adjusted so that the user just perceives the reference signal and subsequently a series of narrow-band test signals of at least 70 msecs. duration and with an interval of at least 150 msecs. is presented to the user. The central frequency and level of said signals are variable. The pleasing sound-level of these test signals as a function of the frequency is determined at a constant level of the reference signal.

The invention will be described in more detail with reference to the accompanying drawing which shows an embodiment thereof. In the drawing:

FIG. 1 shows a block diagram of an arrangement for carrying out the method in accordance with the invention, FIGS. 2a and 2b respectively represent the variation of the sound level of the reference signal and of the test signals as a function of time, and FIG. 3 is a diagram in which the reference sound-level range and the sound-level characteristics experienced as pleasing by several persons who are hard of hearing are plotted.

In FIG. 1 a signal source 1 supplies a band-limited so-called "white noise" signal in the range from approximately 100 Hz to 10 kHz, i.e. a signal for which the signal energy, averaged over a sufficiently long time in a narrow frequency band within this frequency range, is independent of the frequency position of the frequency band. The output signal of the signal source 1 is applied both to a superposition circuit 2 and to one input of a variable band-pass filter 3. The band-pass filter filters the signal components which are situated in a comparatively narrow frequency band, which substantially corresponds to one-third of an octave, out of the output signal of the reference signal source 1. The central frequency of the band-pass filter 3 is variable, in a manner not shown, by means of an adjusting element 4 which can be controlled by the audiometrist.

The output signal of the band-pass filter 3 is applied to the input of an amplifier 5 whose gain is adjustable by means of an adjusting element 6 and whose output signal is applied to the second input of the superposition circuit 2 via a switching device 8. The switching device 8 at option enables the output signal of the amplifier 5 to be blocked, so that only the signal which is supplied directly by the reference signal source 1 appears at the input of the superposition circuit 2. Alternatively the switching device allows the amplifier output signal to be switched on and off periodically without clicks, as the case may be with statistically distributed intervals. Switching on and off without clicks means that upon switching on, the input signal level reaches the stationary value in a specific time (approximately >10 msecs.) and that upon switching off, the input signal level assumes the value zero or a negligibly small value in approximately the same time. Abrupt switching on and off would give rise to steep transients so that, in addition to the frequency components of the narrow-band signal, further frequency components would be applied to the second input of the superposition circuit 2.

The switching device 8 may, for example, consist of a multiplier circuit 9, having one input that receives the output signal of the amplifier 5 and another input that receives a signal obtained from a switching element 10. The switching element 10 selectively supplies a direct voltage—preferably having the value zero—, which multiplied by the output signal of the amplifier 5 also yields the value zero, or a direct voltage 11. The direct voltage 11 varies periodically between a first voltage level, at which the input signal of the multiplier 9 is transferred completely, and a second level, at which the input signal is blocked, with continuous transitions between these two levels.

In principle, the sequence of the components 3, 5 and 8 may be changed arbitrarily. Specifically, it may be effective to include the variable-gain amplifier 5 after the switching device 8 so that the multiplier circuit 9 need only process signals with a predetermined level. If required, the narrow-band test signal may also be generated by a preferably digital generator.

In the superposition circuit 2 the wide-band signals supplied by the signal source 1 and the series of narrow-band but not purely sinusoidal test signals, which are available at the output of the switching device 8, are superimposed on each other and applied to a loudspeaker arrangement 12. The latter converts the electrical signals into acoustic signals and is located in the same room as the patient, not shown, whose hearing aid is to be adapted. If desired, there may be provided a separate loudspeaker for the narrow-band noise. The superposition circuit 2 may then be dispensed with.

FIG. 2a represents the variation of the level of the signal source 1 as a function of time. It can be seen that the level remains constant during the entire examination. At the beginning of the examination only the wide-band signal from the signal source 1 is presented to the patient. Thus, the switching device 8 is operated so that the narrow-band signal is suppressed. The gain of the hearing aid is then adjusted so that the user just hear the acoustic signal which is produced, hereinafter referred to as the reference signal. The sound level at the location of the patient, i.e. the hearing aid, should then have a constant value, which may be between 40 and 50 dB referred to a sound pressure level of 20 $\mu$Pa. If this value is essentially smaller than 40 dB, the examination may be affected adversely by ambient noise. If the value is substantially greater than 50 dB, psychological side effects (reduced concentration etc.) occur and the usable dynamic range for pleasant hearing is limited (limit of discomfort).

Subsequently, the switching device 8 is changed over so that the narrow-band signal becomes audible at intervals. The variation of the level of these signals as a function of time is represented in FIG. 2b. This Figure shows that the narrow-band signal is audible at a predetermined level for a time $T_1$ and is suppressed for the time $T_2$, the transition from one state to the other being smooth. The time $T_1$ during which the narrow-band signals are audible should be between 40 msecs. and 500 msecs., preferably 100 msecs. When $T_1$ is shorter than 70 msecs., there is a risk that the ear has not yet adapted itself to the narrow-band signal, hereinafter referred to as the test signal. However, if the test signal lasts substantially longer than 500 msecs., fatigue effects on the ear may invalidate the test. The intervals between two test signals should be longer than the durations of the actual test signals and should lie between approximately 150 msecs. and 500 msecs.

At a given frequency (i.e. a given setting of the adjusting element 4; FIG. 1) the volume is changed (by means of adjusting element 6) and the patient indicates which level is experienced as a pleasing sound level of speech. This level is determined as the arithmetic mean of the level at which the test signal is experienced as too loud by the patient and the level at which the test level is experienced as too soft by the patient. As the reference signal also remains audible during this second step of the method, a well-defined background noise is obtained, yielding reproducible results. The test signals and the intervals between the test signals have a speech-like nature so that the present method provides an adaptation which under normal conditions of use also ensures that the user will understand speech in an optimum manner.

Subsequently, the pleasing sound level at a different frequency is determined etc. The results thus obtained may be plotted in a diagram by the examiner, as is shown in FIG. 3, the sound level in dB being plotted on the ordinate and the frequency in kHz on the abscissa (quasi-logarithmic). The sound-level range which is pleasing for persons with normal hearing abilities has been pre-printed on this diagram. This range can be determined by testing a number of persons aged younger than 25 years and with unimpaired hearing (to be ascertained in advance by audiological tests) to indicate the optimum sound levels of speech for the various frequencies and at the same reference signal level as that of the persons to be subsequently tested and who are hard of hearing. It is found that for persons with normal hearing abilities the optimum sound level of speech at a reference signal level of for example 50 dB lies at approximately 80 dB with a spread of $\pm 5$ dB. This applies at least to frequencies up to approximately 5 kHz. When the reference signal level is lower, for example 40 dB, the sound level range 15 experienced as pleasing by persons with normal hearing abilities is also situated at lower sound levels.

When the examiner has plotted the sound-level values experienced as pleasing by the patient in the diagram of FIG. 3, a curve is obtained which is characteristic of the quality of the adaptation of the transmission characteristics of the hearing aid to the hearing defect of the user. In principle, three cases may then occur:

(1) The characteristic lies in the sound-level range 15. In this case the adaptation of the hearing aid is already optimum.

(2) The characteristic lies below the sound-level range 15 of a person with normal hearing abilities, i.e. at higher sound levels, such as for example the curve 16 in FIG. 3. Thus, the user of the hearing aid experiences levels as pleasant which are substantially higher than those for persons with normal hearing abilities. In this case the examiner should increase the gain of the hearing aid by approximately the difference between the middle of the volume range 15 and the characteristic 16. If, moreover, this difference is highly frequency-dependent, as in the case of the curve 16 of FIG. 3, where the sound level at frequencies below 1 kHz experienced as pleasing by the patient substantially corresponds to the sound-level range 15 of persons with normal hearing abilities, whereas there is a great difference at the higher frequencies, a frequency-dependent correction by an appropriate change of the filter adjustment is necessary. For example, in the case of the curve 16 either the low frequencies must be attenuated or the high frequencies must be boosted in order to shift the curve 16 into the sound-level range 15 after a suitable change of the gain.

(3) The characteristic lies above the sound-level range experienced as pleasant by persons with normal hearing abilities, i.e. at lower sound levels, such as the characteristic 17 in FIG. 3. It follows that the patient needs a hearing aid with gain control because a sound-level of speech that would be called pleasant by a person with normal hearing abilities is experienced as too loud by him. The gain control ensures that the acoustic gain of the hearing aid is reduced for signals with a higher level in comparison with the gain of signals with a lower level.

In cases (2) and (3) the method should be repeated after changing the gain setting or the gain control until the characteristic is situated as far as possible within the sound-level range 15 experienced as pleasant.

In principle, it is not necessary for the examiner to plot the values in a diagram. The corresponding values may for example be entered directly into an electronic memory by the adjusting elements 4 and 6 after actuation of a storage button. In conjunction with a computer in which the optimum sound-level range 15 is stored, the difference between the characteristics 16 and 17 and the middle of the sound-level range 15, experienced as pleasant by persons with normal hearing abilities, can then be determined as a function of the frequency. The output is displayed by means of a printer or display. Alternatively, semi-automatic recording is possible, as employed in audiometry, for example in accordance with U.S. Pat. No. 4,109,106.

What is claimed is:

1. A method of adjusting a hearing aid by means of a series of acoustic test signals of variable frequency and sound-level for determining the sound-level which is pleasing to the user of the hearing aid as a function of the frequency as compared to a reference sound-level range which is pleasing to persons with normal hearing abilities, after which the gain of the hearing aid as a function of the frequency may be changed so that the sound level found to be pleasing corresponds to the reference sound-level, the method comprising first presenting a wide-band reference signal of predetermined constant level to the user, adjusting the gain of the hearing aid so that the user just perceives the reference signal, subsequently presenting to the user a series of narrow-band test signals of at least 70 msecs. duration and with an interval therebetween of at least 150 msecs., the central frequency and sound level of said test signals being variable, and determining the pleasing sound level of said test signals as a function of the frequency at a constant level of the reference signal.

2. An apparatus for adjusting a hearing aid by means of a series of acoustic test signals of variable frequency and sound level comprising, a reference signal source which generates electrical wide-band signals of constant level, a test signal source which can be switched on together with the reference signal source and which generates an intermittent series of electrical narrow band signals and including adjusting elements for adjusting the frequency and level of the narrow-band signals, and an electro-acoustic transducer which converts the electrical signals into acoustic signals.

3. An apparatus as claimed in claim 2 wherein the test signal source for the generation of the narrow-band signals includes a narrow-band filter with a variable central frequency, means for applying signals from the reference signal source to said narrow-band filter, and the test signal source further comprises a switching device by means of which the narrow-band signals are switched on and off without clicks.

4. An apparatus as claimed in claim 3 wherein the test signal source comprises a variable gain amplifier for adjusting the level of said narrow-band signals, and further comprising means for coupling said filter, said amplifier and said switching device in cascade arrangement between the output of the reference signal source and an input of the electroacoustic transducer, and means for coupling the output of the reference signal source to the input of the electro-acoustic transducer via a separate electric path that is essentially in parallel with said cascade arrangement.

5. An apparatus for adjusting a hearing aid comprising, a source of reference signal for generating electric wide-band signals of constant level, electro-acoustic transducer means for converting electric signals into acoustic sounds, means for coupling an output of the reference signal source to an input of the transducer means, a test signal source for generating a series of electric narrow band signals and including means for adjusting the center frequency and the level of said narrow band signals, and means for selectively coupling said test signal source to the input of the transducer means.

6. An apparatus as claimed in claim 5 wherein the test signal source comprises, a narrow-band filter with means for varying the center frequency thereof, a variable gain amplifier, said selective coupling means comprising a switching device, and means for coupling the amplifier and the switching device in cascade with the filter between the output of the reference signal source and the input of the electro-acoustic transducer means.

7. An apparatus as claimed in claim 5 wherein the selective coupling means comprises a switching device operative to pass a series of pulse type narrow-band test signals exhibiting a smooth transition of the pulse waveform between the on and off states of the switching device, and wherein the on state has a time duration of at least 70 msecs and the off state has a time duration longer than the on state time duration.

8. A method of adjusting a hearing aid in relation to a reference sound level range which is comfortable for persons with normal hearing comprising, deriving a wide-band electric reference signal of constant level, supplying said reference signal to an electro-acoustic transducer, adjusting the gain of the hearing aid so that the person wearing it can just perceive the acoustic reference signal developed by the transducer, deriving a series of narrow-band test signals of at least 70 msecs. duration and with a time interval therebetween of at least the duration of the test signals, subsequently applying said test signals to the transducer simultaneously with said reference signal, and varying the center frequency and level of said test signals to determine a comfortable sound level of said test signals as a function of the frequency and at a constant level of the reference signal.

* * * * *